United States Patent [19]
Enderlin et al.

[11] Patent Number: 4,911,002
[45] Date of Patent: Mar. 27, 1990

[54] LOGGING APPARATUS FOR A CORE SAMPLE CUTTER

[75] Inventors: Milton B. Enderlin, Arlington; Keith Vickers, Crowley; Thomas Knode, Fort Worth, all of Tex.

[73] Assignee: Halliburton Logging Services Inc., Houston, Tex.

[21] Appl. No.: 334,054

[22] Filed: Apr. 6, 1989

[51] Int. Cl.[4] ............................................. E21B 49/00
[52] U.S. Cl. ........................................ 73/153; 73/660; 51/165.71; 125/13 R; 318/490
[58] Field of Search ..................... 73/153, 864.41, 660; 125/13 R; 51/165 R, 165.71, 165.74; 83/471.2, 471, 522; 340/680, 683; 346/25, 33 MC; 318/490

[56] References Cited

U.S. PATENT DOCUMENTS

| | | | |
|---|---|---|---|
| 4,372,174 | 2/1983 | Cymbalisty et al. | 73/863.11 |
| 4,527,101 | 7/1985 | Zavis et al. | 318/490 |
| 4,537,177 | 8/1985 | Steere, Jr. et al. | 125/13 R |
| 4,559,600 | 12/1985 | Rao | 340/680 |
| 4,744,242 | 5/1988 | Anderson et al. | 340/683 |

Primary Examiner—Hezron E. Williams
Assistant Examiner—Kevin D. O'Shea
Attorney, Agent, or Firm—William J. Beard

[57] ABSTRACT

Measuring apparatus for use with a motor driven rotary saw blade is disclosed so that dynamic measurements can be obtained while cutting lengthwise a core sample from a well borehole. The core sample is held, and the motor driven rotary driven saw blade is used to cut along the length of the core sample. Selected transducers are installed, and all the transducers connect to a CPU which also has connections with a clock, memory and recorder. Data is recorded either as a function of time or as a function of the location of the cutting tool along the core sample. Transducers include a current monitor for current operating the motor, a microphone measuring sound levels generated by the saw blade cutting through the core sample, a tension measuring device which provides the force which causes the motor to traverse along the length of the core sample, and also X, Y, Z coordinate vibration sensors such as accelerometers. Another measuring device responds to the force applied to the motor causing it to move, and the relative position of the saw blade relative to the disk is also measured.

16 Claims, 1 Drawing Sheet

LOGGING APPARATUS FOR A CORE SAMPLE CUTTER

BACKGROUND OF THE DISCLOSURE

One of the oil well completion techniques used in determining which, if any, completion procedures are to be applied to the well involves taking a cylindrical rock core. Moreover, the rock core can provide additional data which is important to selection of a particular completion technique. It is not uncommon to cut a long cylindrical rock core or core sample from a well at an intermediate stage during drilling. Often, a cutting tool is lowered into the well so that a sample up to several feet in length is obtained. It is typically removed to a laboratory where certain tests are run on the sample. Many measurements can be taken such as permeability, porosity, and the like. In addition, other measurements are taken of physical parameters such as weight and density. After many physical measurements are obtained from the core sample, it is not uncommon to slice the core sample lengthwise to thereby obtain two halves, separated by a diametrical cut, and other inspection techniques may well be practiced on the facing diametrical faces.

For the latter purpose, a saw is normally required to cut through the core sample. The core sample must be held by an alignment tool so that the saw can proceed along the length of the core sample to form the cut. As the cut is made, the resistance of the core sample to cutting will be observed. The present apparatus provides a log of cutting the core sample. This log enables additional analysis to be obtained from the core sample. For instance, it permits plotting of the resistance of the core sample to cutting as the cut is made so that variations along the length of the core sample are noted. This is particularly useful to provide an indication of strength, brittleness, and other factors which relate to the mechanical properties of the core sample.

The present apparatus is thus adapted to be used with a motor driven rock cutting saw blade. Various indicators are measured so that the brittleness, strength, and hardness of the core sample can be determined. The present apparatus includes X, Y and Z vibration sensors which are accelermeters mounted on the motor. Vibration is imparted to the motor from the chatter of the saw blade as it cuts through the core sample. In addition, the motor current is monitored to obtain another output. The motor is advanced during cutting, therebeing a weight mechanism to pull the motor along the core sample, and the tension imparted to the motor is thus also recorded. The position of the motor along the core sample is likewise recorded. A microphone is included at a fixed location relative to the motor to record the sound level during cutting. All of this data is input to a CPU and then to a recorder where it is recorded as a function of time. As will be discussed hereinafter, physical properties of the core sample can be determined after cutting.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
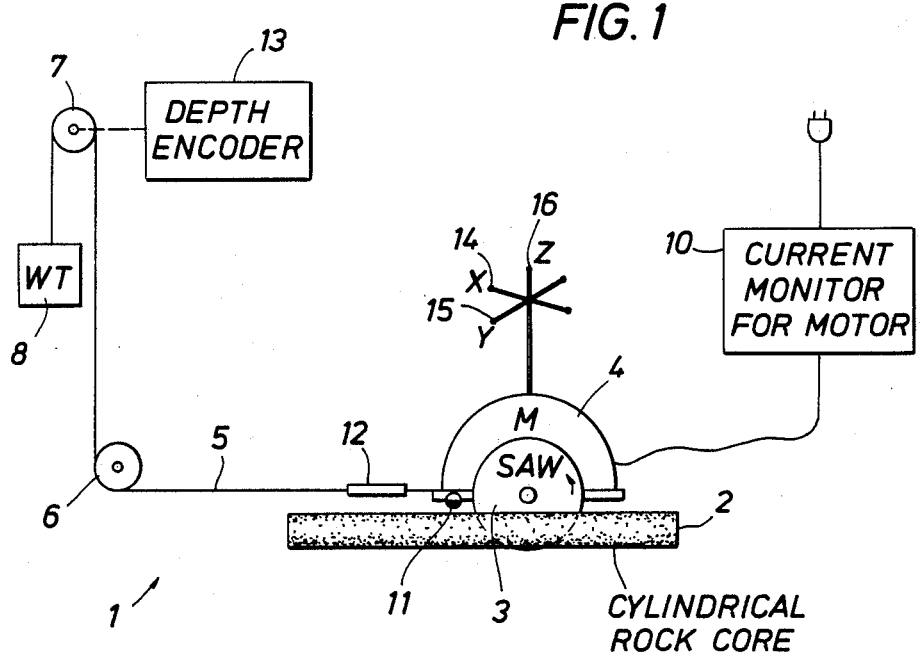
FIG. 1 shows a core sample cutting saw with motor and further illustrates transducers connected thereto for obtaining dynamically data created during cutting of the core sample.
Figure 2:
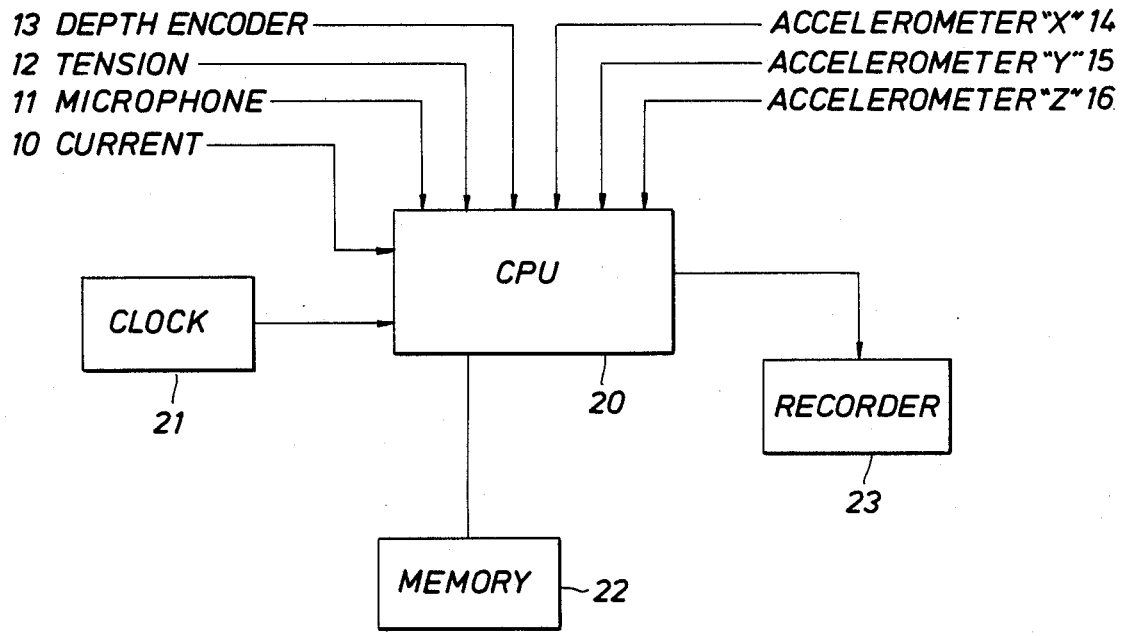
FIG. 2 is an electronic schematic of the transducers which measure data during cutting and which data is input to the system shown in FIG. 2 for analysis and recording.

Attention is now directed to FIG. 1 of the drawings where the core sample cutting apparatus of the present disclosure is illustrated. In FIG. 1, the cutting system is generally identified by the numeral 1 and utilizes a support table (omitted for the sake of clarity) for holding a core sample of any length. The core sample 2 is supported on a table for cutting by a rock cutter having the form of a saw blade 3. The saw blade is powered by the motor 4, and cuts the core sample as the blade is advanced through the sample. The motor is supported relative to the core sample 2 to cut the full length of the sample and is advanced from right to left as viewed in FIG. 1 of the drawings. It is pulled by a cable 5 which passes over a pulley 6 and a second pulley 7. In turn, the cable 5 connects to a weight 8 which pulls the motor with a specified force determined by the weight. Obviously, the motor will travel more rapidly during cutting of certain samples; other samples require longer to cut and the motor will travel more slowly.

The numeral 10 identifies a first sensor which is a current monitor for the motor current. That provides a signal encoding the current flow to the motor during its operation. A microphone 11 is mounted on the support structure for the motor, and is positioned at a fixed distance from the cutter 3. In other words, it is located at a fixed distance so that sound levels are recorded with a common attenuation between the noise source and the microphone 11. Tension in the cable is measured by a strain gauge transducer 12 which is installed in the cable. This provides an output indicative of tension on the cable and hence the force to the motor which moves the motor and associated saw 3 while cutting the core sample 2. A depth encoder 13 is also included. As the pulley 7 is rotated, the encoder 13 forms a signal indicative of the location of the cutter 3 along the sample 2. The core sample is thus placed at a known location, and as cutting occurs, the location of the cutter relative to the core sample is output by the depth encoder 13. Depth is indicated relative to the well borehole. The core sample as shown in FIG. 1 located horizontally for convenience in cutting. In actuality, the core sample is obtained from a well which is more or less drilled vertically, and in that sense, the encoder 13 provides an indication of the depth in the borehole where the cut actually occurs. As an example, if the core sample were twelve feet in length, the encoder 13 would provide an indication that the cut proceeded from a well depth of 5,000 feet to 5,012 assuming the core sample was cut from that depth.

There are X, Y and Z vibration sensors which are indicated at 14, 15 and 16 also included, and these three sensors form the additional outputs as will be noted.

The several outputs are provided to a CPU 20. That cooperates with a clock 21. Appropriate scale factors and the like are stored in memory at 22. The data is formatted and output to a recorder 23 as a function of time. It can be rearranged to be a function of other variables, discussed below.

Operation of this apparatus should be first reviewed. Briefly, the apparatus has a time base recorder. This can take the form of a strip recorder in most uses. As the cut is made, the several variables can simply be recorded and displayed on the strip chart recorder 23 so that they can be analyzed as a function of time. Another mode of presentation of the data is to record and present the data as a function of the depth in the well borehole. Again using the example given above, assume that the core sample is twelve feet in length and extends from a depth of 5,000 feet in the borehole. With this depth signal provided from the sensor 13, it can be scaled so that all the variables at particular depths relative to the borehole are encoded. This may show various and sundry mechanical characteristics relating to the core sample 2. When this occurs, the physical characteristics of the core sample can be more readily analyzed and identified with one or more strata. Consider as an easy example a marked change in hardness as a function of depth in the borehole. Where the core sample is relatively soft, the saw blade 3 will advance rapidly. When the hard portion is encountered, the noise level will change which is sensed by the microphone 11. The current measured by the current monitor 10 will also show a change. There will be a different type vibration experienced by the motor. This will be shown by the three accelerometers. On traversing from a soft material to a hard material, the rate of advance is changed. It will take longer to cut through a hard material compared to an equal thickness of soft material. That also is shown by the recorded data. In summary, all the data is displayed by the strip chart recorder, and data interpretation can be obtained therefrom indicative of physical characteristics of the core sample 2 such as strength of the core sample in different dimensions, Young's modulus, and any other physical variable that is of interest. Suitable constants are stored in the memory 22 to convert the measured values into physical parameters such as Young's modulus. This can be accomplished by utilizing core samples of known strength as calibration standards whereby they are cut and their data is recorded. It is especially important to utilize fixed standards. That is, certain variables are fixed so they will not impact the variables. One such important variable is the diameter of the core sample which is preferably fixed. That is, a set of data is collected for a given size core sample. If larger samples are obtained, they will modify the data during cutting even though they may be from the same rock. The same size motor is used, and special attention is given to the cutter 3 which is also preferably fixed. It is particularly important that the cutter in every use have an initial dressing so that they perform identically. Last of all, the motor is operated with the same speed and same torque for all tests. When these variables are fixed, the only variables which are left are those which can indicate strength of the core material itself free of error resulting from the lack of stability in initial conditions.

In summary, a core sawing system which provides dynamically made measurements arising from the act of cutting the core sample is disclosed. These variables are utilized to enable variable conversion into physical measurements of the core sample, typically being measurements related to strength of the rock.

While the foregoing is directed to the preferred embodiment, the scope thereof is determined by the claims which follow.

What is claimed is:

1. For use with a motor powered saw for cutting an elongate core sample, an apparatus which comprises sensor means for detecting operation of the motor as the motor cuts the core sample with a saw blade, and means connected to said sensor means for obtaining the signal therefrom to form a record thereof during cutting of the core sample.

2. The apparatus of claim 1 including a clock means connected to means for forming a time based record as the core sample is cut along the length thereof.

3. The apparatus of claim 1 wherein said sensor means includes means for measuring the current flow to the motor during cutting of the core sample.

4. The apparatus of claim 1 wherein said sensor means includes means for measuring the vibrations from the motor during cutting of the core sample.

5. The apparatus of claim 1 wherein said sensor means includes means for measuring the sound level generated by the saw during cutting of the core sample.

6. The apparatus of claim 1 wherein said sensor means includes means for measuring the force moving said motor during cutting of the core sample.

7. The apparatus of claim 1 wherein said sensor means includes means for measuring the relative position of the motor and associated saw blade with respect to the core sample.

8. The apparatus of claim 1 including a CPU connected to said sensor means for receiving signals therefrom, and means for recording said signals as a function of time.

9. The apparatus of claim 1 including a CPU connected to said sensor means for receiving signals therefrom, and means for recording said signals as a function of length along the core sample.

10. The apparatus of claim 1 wherein said sensor means forms an output signal and said output signal is input to a CPU and is converted into an indication of physical characteristics describing the strength of the core sample material.

11. A method of measuring physical characteristics of a core sample comprising the steps of:
    (a) positioning a motor driven rotary saw blade for cutting a core sample;
    (b) cutting the core sample with the saw blade along he length of the core sample;
    (c) during cutting, measuring operation of the motor driven saw blade to obtain over a period of time such measurements; and
    (d) as a function of such measurements determining the strength of the core sample.

12. The method of claim 10 including the step of measuring electric current required for operation of the motor during cutting.

13. The method of claim 10 including the step of measuring motor vibration required for operation of the motor during cutting.

14. The method of claim 10 including the step of measuring sound from operation of the core sample cutting blade required for operation of the motor during cutting.

15. The method of claim 10 including the step of measuring force applied to the motor required for operation of the motor during cutting.

16. The method of claim 10 including the step of measuring location of the motor with respect to the core sample as it traverses the length of the core sample during cutting.

* * * * *